United States Patent [19]

Ragsdale

[11] Patent Number: 4,750,100
[45] Date of Patent: Jun. 7, 1988

[54] TRANSFECTION HIGH VOLTAGE CONTROLLER

[75] Inventor: Charles W. Ragsdale, Concord, Calif.

[73] Assignee: Bio-Rad Laboratories, Richmond, Calif.

[21] Appl. No.: 872,060

[22] Filed: Jun. 6, 1986

[51] Int. Cl.⁴ .............................................. H02M 7/04
[52] U.S. Cl. ..................................... 363/86; 363/68; 323/271; 361/56; 361/91
[58] Field of Search ..................... 363/68, 85, 86, 89, 363/96; 323/271; 307/252 L, 252 Q; 361/56, 91, 100, 111

[56] References Cited

U.S. PATENT DOCUMENTS

| | | | |
|---|---|---|---|
| 3,609,413 | 9/1971 | Lane | 361/91 |
| 3,772,532 | 11/1973 | Petrov et al. | 307/252 L |
| 3,898,410 | 8/1975 | Peters, Jr. | 363/96 |
| 4,489,372 | 12/1984 | Hatano et al. | 363/68 |
| 4,571,535 | 2/1986 | Gyugyi | 363/68 |

FOREIGN PATENT DOCUMENTS

| | | |
|---|---|---|
| 644347 | 10/1950 | United Kingdom . |
| 967569 | 8/1964 | United Kingdom . |
| 1198111 | 7/1970 | United Kingdom . |
| 1459654 | 12/1976 | United Kingdom . |
| 1476647 | 6/1977 | United Kingdom . |
| 2000919A | 1/1979 | United Kingdom . |
| 2075759A | 3/1981 | United Kingdom . |
| 1598590 | 9/1981 | United Kingdom . |

OTHER PUBLICATIONS

"SCR Manual Including Triacs and Other Thyristors", Fifth Edition, 1972, General Electric Company, pp. 159–164.
"Solid State Device Manual," 1975, RCA Corporation, pp. 16–18.

Primary Examiner—Patrick R. Salce
Assistant Examiner—Anita M. Ault
Attorney, Agent, or Firm—Townsend and Townsend

[57] ABSTRACT

A transfection high-voltage controller for directing high-voltage currents to a suspension of cells and DNA comprising a control section, a power store, and a high-joule switch. Under control of the control section, the high-joule switch directs a high-voltage current from the power store to a load such as a cuvette. The high-joule switch comprises a semiconductor controlled rectifier (SCR) having a gate coupled to the control unit for triggering the device, an anode for receiving the high-voltage current from the power store, and a cathode for delivering the high-voltage current to the cuvette. A current sink may be connected to the anode of the SCR to render it non-conductive a predetermined time after the high-voltage current appears at the cathode. Multiple SCRs may be connected in series to support voltages over 3,000 and currents in excess of 125 amperes, and a trigger control unit may be attached to the gate of each SCR in the series to effect simultaneous or serial triggering of the group.

35 Claims, 5 Drawing Sheets

TRANSFECTION HIGH VOLTAGE CONTROLLER

BACKGROUND OF THE INVENTION

The invention relates generally to transfection and cell fusion and, more particularly, to a method and apparatus for directing high-voltage currents to a suspension of cells and DNA.

In the biotechnical field, it is sometimes desirable to introduce cloned DNA into mammalian and any other cells using a high-voltage electrical discharge. This method, commonly referred to as "transfection," typically involves creating a suspension of cells in a phosphate-buffered saline (PBS) solution and adding cloned DNA. The suspension is then subjected to a highvoltage pulse from a pulse generator of some kind which causes the cells to take up and express the exogenous DNA. Various pulse generators are available for this purpose, and most supply current in the milliampere range. One unit is available which can apparently produce 40 amperes of current.

The amount of voltage and current required in transfection procedures depends upon the cell and DNA types, and the electrical characteristics must be closely controlled. It has been discovered that some transfection procedures require currents of as much as 125 amps and more. This current requirement is vastly greater than that available from known pulse generators in the biotechnology field.

Known power supplies used in the biotechnology field are incapable of deliverying the required current, and they could not be modified to do so because such power supplies are transistor-driven, and transistors are capable of providing only up to approximately 50 amperes of current. Known power supplies with the capability of generating such high currents are unsuitable for biotechnology applications since they are cost-prohibitive and do not have adequate safety control mechanisms. For example, they are often not designed for frequent human manipulation, and a risk of shock is usually present. A shock from these devices would most likely be lethal.

Even if a high-current power supply is constructed, it must be capable of generating high voltage, high energy, rectangular pulses. Switching the components in such a high-voltage/high-current power supply to create the rectangular pulses is likely to create severe stress on the components and possibly cause damage to the power supply.

SUMMARY OF THE INVENTION

The present invention is a transfection highvoltage controller using semiconductor controlled rectifiers (SCR's) for directing a high voltage current to a suspension of cells and DNA. The invention is capable of supplying voltages in excess of 3,000 volts and currents in excess of 125 amps with relative safety. In addition, the invention is capable of producing highvoltage/high-energy exponential or rectangular pulses with minimum stress on the switching components.

In one embodiment of the present invention, a high-joule switch is triggered by a control unit and directs a high-voltage, high-current pulse from a capacitor in a power storage module to a cuvette. The high-joule switch comprises a semiconductor controlled rectifier (SCR) which has its anode coupled to the high-voltage capacitor and its cathode coupled to the cuvette. The gate of the SCR is coupled to the control unit and is triggered thereby.

The control unit controls the charging of the high-voltage capacitor through an alternating current switch. When the capacitor charges up to a selected voltage, the control unit activates a trigger unit which emits a voltage pulse to the gate of the SCR. The pulse emitted by the trigger unit renders the SCR conductive, and the SCR directs the current from the high-voltage capacitor to the cuvette.

To generate high-voltage/high-energy rectangular pulses, the invention exploits the fact that an SCR is rendered non-conductive whenever the current flowing into its anode falls below a minimum value termed "the holding current." A current sink is coupled to the anode of the SCR for substantially instantaneously reducing the current therein below the SCRs rated holding current at a predetermined interval of time after the high-voltage curent appears at the cathode of the SCR. The substantially instantaneous turn-off of the SCR which results produces the falling edge of the desired rectangular pulse. The square top required for a square wave is produced if the desired pulse duration is short compared to the exponential fall of the capacitor voltage.

To enhance operating flexibility and provide for increased voltage capabilities, a plurality of highjoule switches may be connected in series to create an array of SCRs for producing a desired voltage/current combination. A trigger control module is connected to each gate of the plurality of SCRs for simultaneous or serial triggering of each SCR as the circumstance requires.

To enhance safety of the device, a novel shunting circuit comprising static and dynamic voltage equalizers is placed across the anode and the cathode of a single SCR or each SCR in an array. The shunting circuit is, in turn, connected to a series of resistors, so that the cathode (output) of a single SCR or the last SCR in an array is connected to a point between the shunting circuit and the series of resistors. Each steady-state voltage equalizing circuit comprises a resistor which proportions the maximum steady-state voltage that can exist across each SCR in an array. Each dynamic voltage equalizing circuit comprises a metal oxide varistor in series with a capacitor for effectively decoupling the dynamic equalizing circuit from the steady-state equalizing circuit. Decoupling the circuits ensures that the dynamic voltage equalizing circuit does not contribute to the resistance of the steady-state voltage equalizing circuit. Therefore, the resistors in the steady-state voltage equalizing circuit contribute their full resistance to and create with the aforementioned series of resistors at the circuit output a voltage divider which limits the voltage existing at the cathode of the single SCR or the last SCR in an array. The voltage at the cathode of the single SCR the or last SCR in the array controls the voltage at which the SCR may be triggered, so the safety circuit helps to prevent the possibility that a person touching the output terminals of the pulse generator may inadvertently be shocked should the SCRs be triggered.

The invention will be better understood by reference to the following detailed description when taken in conjunction with the accompanying drawings.

DESCRIPTION OF THE PREFERRED EMBODIMENTS

The Basic Circuit

Figure 1:
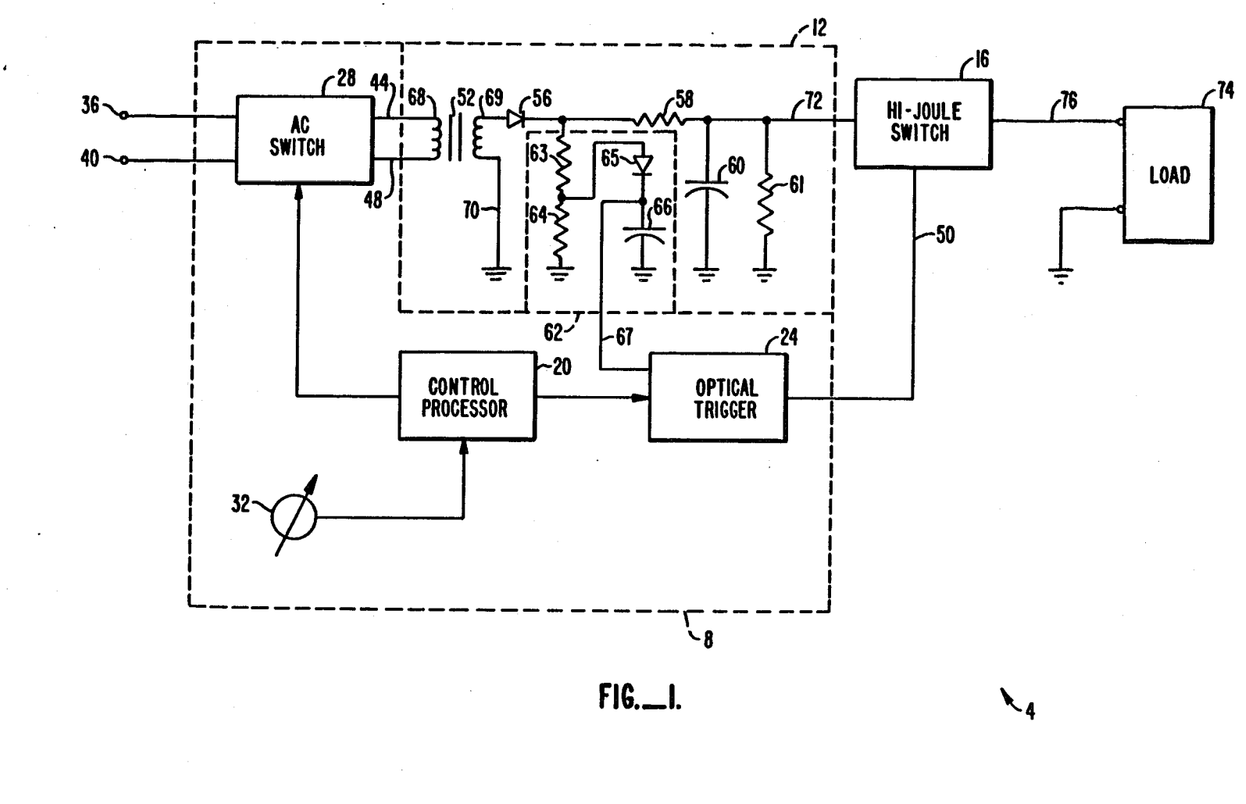
FIG. 1 is a diagram of a transfection highvoltage controller which produces exponential pulses according to the invention.

FIG. 1 shows the novel transfection highvoltage controller 4 for producing exponential pulses. Voltage controller 4 comprises a control section 8, a power store 12, and a high-joule switch 16.

Control section 8 comprises a control processor 20 which is connected to both an optical trigger 24 and an AC switch 28. Control processor 20 may comprise programmable microprocessors, such as a Motorola Part No. MC68705, or analog/combinational logic and is for controlling the operation of optical trigger 24 and AC switch 28. Control processor 20 may be manually controlled by a manual control unit 32. AC switch 28 receives alternating current from AC inputs 36 and 40 and provides alternating current to power store 12 through current lines 44 and 48. Optical trigger 24 is for triggering high-joule switch 16 and is connected to high-joule switch 16 by a trigger line 50. Optical trigger 24 may comprise a light-activated semiconductor-controlled rectifier (LASCR) of well known construction so that control processor 20 need not supply the higher voltage normally required to activate high-joule switch 16.

Power store 12 comprises a transformer 52, a diode 56, a resistor 58, a capacitor 60, and a resistor 61 for supplying power to high-joule switch 16. Power store 12 also includes a trigger feed circuit 62 for supplying trigger energy for optical trigger 24. Trigger feed circuit 62 comprises a resistor 63 connected to the cathode of diode 56, a resistor 64 connected in series with resistor 63, a diode 65 connected to a node between resistors 63 and 64, and a capacitor 66 connected in seris with diode 65. A trigger feed line 67 is connected to the cathode of diode 65 for supplying trigger energy to optical trigger 24. Trigger feed circuit 62 eliminates the need for a special power supply for optical trigger 24 and allows optical trigger 24 to automatically adjust for the varying operating conditions of high-joule switch 16.

The low voltage winding 68 of transformer 52 is connected to current lines 44 and 48. The high-voltage winding 69 of transformer 52 is coupled to a ground line 70 and to a diode 56. Diode 56 is for rectifying the current flowing from transformer 52 and is connected to resistor 63 of trigger feed circuit 62 and through resistor 58 to capacitor 60, resistor 61, and a switch-input line 72 of high-joule switch 16, respectively. Capacitor 60 is charged to a high-voltage level by the current flowing from the high-voltage winding 69 of transformer 52 and is for supplying a high-voltage current to highjoule switch 16. Resistor 58 is for limiting current to capacitor 60 so that a small transformer 52 may be used. Resistor 61 is for gradually discharging capacitor 60 for reasons which shall be discussed in greater detail below.

When closed, high-joule switch 16 directs substantially all charge/energy from capacitor 60 to a load 74, such as a cuvette, through a load-line 76. Capacitor 60 discharges exponentially thereby producing an exponential output waveform.

Figure 2:
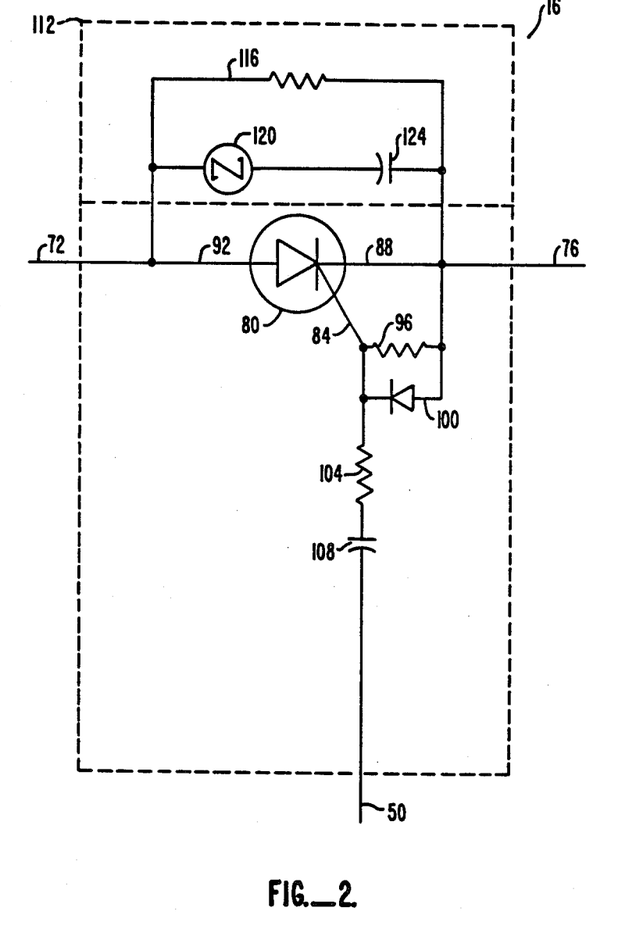
FIG. 2 is a schematic diagram of an embodiment of the high-joule switch of FIG. 1.

FIG. 2 is a schematic of one embodiment of high-joule switch 16. The major switching element in high-joule switch 16 is a semiconductor controlled rectifier (SCR) 80 having a gate 84 for triggering the operation of SCR 80, a cathode 88 for providing high-voltage current to load-line 76, and an anode 92 for receiving high-voltage current from switch input line 72. As used herein, a semiconductor controlled rectifier designates any reverse-blocking triode-thyristor. The name of the actual semiconductor material used in the manufacture of the device (silicon, selenium, etc.) may be substituted in place of the word "semiconductor," and it is intended that the invention encompass all such embodiments of the device. For the purpose of example, a silicon-controlled rectifier, such as part number 2N3899 manufactured by General Electric Company, may be used for SCR 80.

Coupled to gate 84 and cathode 88 of SCR 80 is a resistor 96 for ensuring that gate 84 and cathode 88 are at the same electrical potential for triggering. A diode 100 is for ensuring that gate 84 and cathode 88 are never reverse-biased. Also connected to gate 84 is a resistor 104 for limiting current to gate 84 and a capacitor 108 for coupling and blocking a high voltage in the switch from appearing on trigger line 50.

A shunt circuit 112 is connected to cathode 88 and anode 92 for shunting SCR 80 during static and dynamic states. A resistor 116 is for shunting SCR 80 during steady states and for dividing the voltage across each SCR 80 when multiple SCRs are coupled to form a multi-switch high-current circuit as described below. A metal oxide varistor 120 is connected in series with a capacitor 124 for shunting SCR 80 during triggering and other dynamic states.

In operation a low-voltage alternating current supply (not shown) is connected to AC inputs 36 and 40 (FIG. 1). A desired voltage is set, and circuit operation is begun by manipulating manual control unit 32. Control processor 20 closes AC switch 28 which thereupon directs AC voltage to the low-voltage winding 68 of transformer 52. Transformer 52 produces a high-voltage alternating current at high-voltage winding 69 which is rectified by diode 56 for charging capacitor 60 through resistor 58. Control processor 20 allows capacitor 60 to charge to a voltage above the prescribed voltage set by manual control unit 32 without triggering high-joule switch 16 for eliminating the potential effects of a delay in AC switch 28 which could cause erratic triggering of high-joule switch 16.

After capacitor 60 has charged to a voltage sufficiently above the prescribed voltage, control processor 20 opens AC switch 28, and capacitor 60 gradually discharges through resistor 61. When the charge on capacitor 60 reaches the voltage prescribed by manual control unit 32, control processor 20 transmits an optical pulse to optical trigger 24 which, in turn, uses the energy from trigger feed circuit 62 to generate an electrical pulse through trigger line 50 and to high-joule switch 16. Resistor 104 and capacitor 108 of FIG. 2 supply sufficient voltage and current and for a sufficient duration to initiate sustained operation of SCR 80, and the charge and energy existing on capacitor 60 are allowed to pass from anode 92, to cathode 88 to load-line 76 and thence to load 74.

Multi-Switch High-Current Circuit

The construction of high-joule switch 16 allows multiple switches to be placed in series in order to obtain high currents in excess of 100 amps at 3,000 volts. This is desirable since many transfection applications require such high currents, and a series of lower capacity SCRs may be coupled and operated for this purpose relatively inexpensively while single high-joule SCRs are very expensive.

Figure 3:
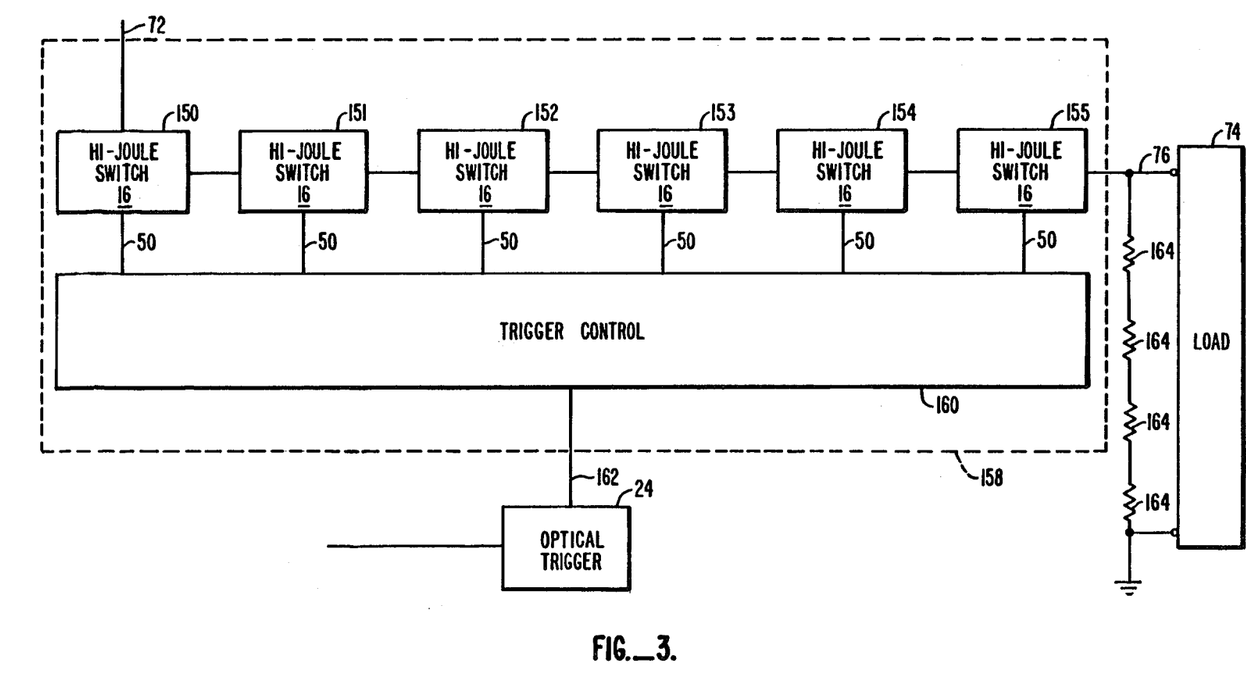
FIG. 3 is a block diagram of a plurality of high-joule switches coupled in series according to the invention.

FIG. 3 depicts a multi-switch high-current circuit 158 comprising a serial configuration of a plurality of high-joule switches 16 and a trigger control 160. The plurality of high-joule switches 16 form a plurality, e.g., six, switch cells 150, 151, 152, 153, 154, and 155. Switch cell 150 is connected to switch input line 72, and switch cell 155 is connected to loadline 76. Trigger control 160 is connected to trigger line 50 of each high-joule switch 16 and interfaces to optical trigger 24 via a trigger drive line 162. Trigger control 160 triggers the plurality of switch cells in response to optical trigger 24. Trigger control 160 may perform either simultaneous or serial triggering of each switch cell as the circumstance requires.

In this embodiment, a plurality, e.g., four, resistors 164 are coupled to load-line 76 and in parallel with load 74 for reasons discussed below.

When the SCRs are in their blocking (non-conducting) states, the difference in blocking characteristics of each device results in unequal steady state voltage sharing. This could be harmful to an SCR with inherently low blocking current since it might cause excessive voltage to appear across the SCR. Accordingly, the shunt resistors 116 act to equalize the voltage across each SCR 80 during steady state. Similarly, when the delay time of one SCR is considerably longer than the other SCRs in the series, full voltage will be momentarily supported by the slow turn-on SCR. The same occurs when the SCRs turn off, since all SCRs will not recover at the same time instant, and the first cell to regain its blocking state will support the full voltage. Accordingly, metal oxide varistor (MOV) 120 and a capacitor 124 in each switch cell equalize the voltage during these periods.

In addition to the voltage equalization function of resistors 116 and each MOV 120/capacitor 124 pair, these components serve an important safety function when considered in conjunction with resistors 164. The impedance of each MOV 120 is very high, and each capacitor 124 essentially acts as an open circuit when each SCR 80 is in the non-conducting state. Thus, the resistance of each MOV 120 does not significantly affect the resistance of resistors 116, and resistors 116, in conjunction with resistors 164, form a voltage divider wherein each resistor 116 contributes substantially its full resistance to the divider circuit. For the purposes of this embodiment, values of 1M ohms for each resistor 116 and 18K ohms for each resistor 164 are recommended.

If a high-resistance load (e.g, a human body) is attached to the system, resistor 116 is each switch cell in conjunction with resistors 164 make the voltage at load line 76, which, in turn, is connected to the cathode 88 of SCR 80 in switch cell 155, too high to allow triggering of that switch cell by trigger control 160. In this embodiment, triggering begins at loads of approximately 1,000 ohms. Reliable triggering occurs with actual sample loads which have a resistance of less than 1,000 ohms, while the human body, which has a resistance of approximately 10K ohms, prevents triggering.

Figure 4:
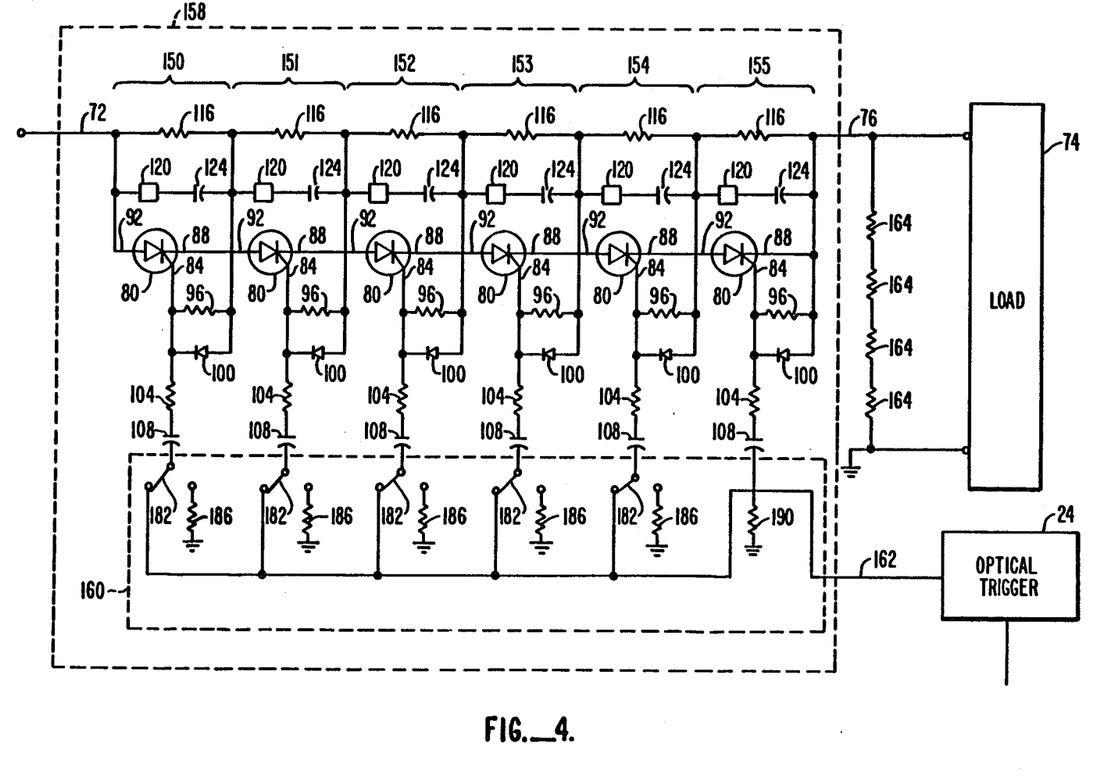
FIG. 4 is a schematic of the embodiment of the invention illustrated in FIG. 3.

FIG. 4 is a detailed schematic of the embodiment of the invention depicted in FIG. 3. The components of each high-joule switch comprising each switch cell are numbered as in FIG. 2.

Trigger control 160 includes a mode switch 182 associated with each switch cell 150, 151, 152, 153, 154, and 155 for setting the desired triggering mode. Mode switches 182 may be either mechanical or electrical switches as desired. Mode switches 182 connect switch cells 150, 151, 152, 153, 154, and 155 to optical trigger 24 when simultaneous triggering is desired.

Trigger control 160 also includes a serial mode resistor 186 associated with each switch cell 150, 151, 152, 153, and 154. Modes switches 182 connect switch cells 150, 151, 152, 153, and 154 to serial mode resistors 186 when serial triggering of the switch cells is desired, and serial mode resistors 186 are, in turn, coupled to a ground potential. Serial mode triggering may be used for the current sink function described for pulse generation below.

Switch cell 155 is not connected to a mode switch 182. Instead, switch cell 155 is always connected to optical trigger 24 and to a resistor 190 which is referenced to a ground potential.

Operation of the multiple switch circuit is essentially the same as described for the basic circuit, except that two triggering modes are available to the operator. For higher voltage, simultaneous triggering, mode switches 182 are connected to optical trigger 24 as shown in FIG. 4. Thus, when optical trigger 24 is activated, a triggering pulse is simultaneously applied to the gate 84 of each SCR 80 in each switch cell, and the switch cells become conductive substantially simultaneously.

For low-voltage triggering and for pulse generation as described below, serial triggering is desirable. For serial triggering, mode switches 182 are positioned to contact serial mode resistors 186. This allows capacitors 108 in each switch cell to charge to a prescribed potential. Additionally, load line 76 is referenced to a substantially ground potential. By referencing load line 76 to a substantially ground potential (which is communicated to the cathode 88 of SCR 80 in switch cell 155), a low-voltage triggering source (not shown) may be used in place of optical trigger 24 when the triggering delay inherent in optical trigger 24 is undesirable. When the low-voltage trigger is activated, it triggers SCR 80 in switch cell 155. When switch cell 155 turns on, the voltage appearing at cathode 88 of SCR 80 in switch cell 154 drops substantially to a ground potential. This near-ground potential causes capacitor 108 in switch cell 154 to discharge, and capacitor 108 supplies sufficient current to the gate 84 of SCR 80 in switch cell 154 to trigger it. The anode 92 of SCR 80 in switch cell 154 then assumes a near-ground potential and the process repeats itself in a ripple effect through switch cells 153, 152, 151, and 150, respectively.

Pulse Generator Circuit

Electrofusion applications require the generation of high-voltage, high-energy rectangular pulses. However, SCRs remain conductive until the principal current flow through the anode is reduced to a level below the specified holding current for the device. Therefore, in order to turn off SCR 80 and to produce a desired rectangular pulse, the current flowing through anode 92 must be reduced below the specified holding current a predetermined time after the high-voltage current appears on load-line 76. Furthermore, the reduction must be substantially instantaneous so that the current flowing through SCR 80 remains substantially the same throughout the pulse duration and so that the failing edge of the pulse is substantially vertical. A pulse generator circuit 191 depicted in FIG. 5 may be used for this purpose. The basic elements of pulse generator circuit 191 are constructed according to the basic circuit shown in FIG. 1, so only the details of the pulse operating mechanism shall be described.

Figure 5:
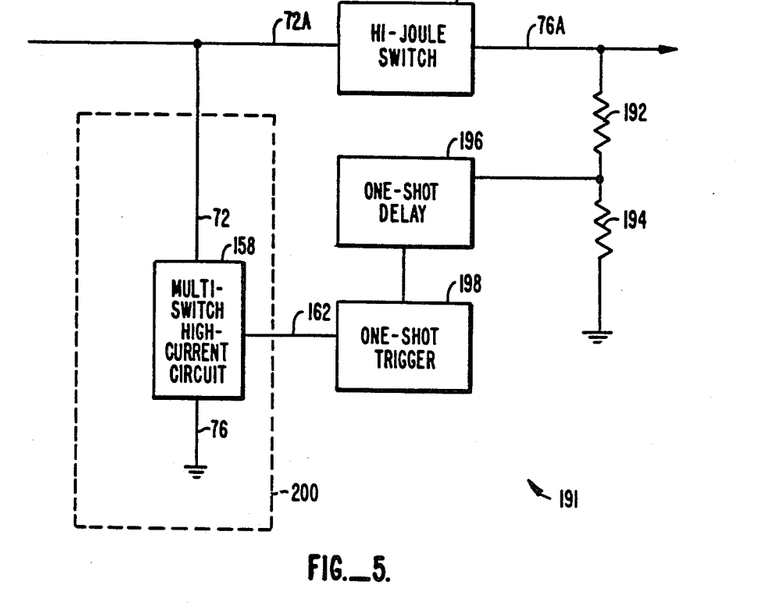
FIG. 5 is a diagram of an apparatus for providing square waves using the high-joule switch of FIG. 1.

As shown in FIG. 5, a load-line 76A of a high-joule switch 16A is connected to resistors 192 and 194. Resistors 192 and 194 are connected in series, and resistor 194 is connected to ground. A one-shot delay 196 of known construction has its input connected to a point between resistors 192 and 194 and its output coupled to a one-shot trigger 198. One-shot trigger 198 is connected to a crowbar 200. The input terminal of crowbar 200 is connected to a switch input line 72A for directing current away from high-joule switch 16A, and the output terminal of crowbar 200 is connected to ground.

As shown in FIG. 5, crowbar 200 may be constructed from the multi-switch high-current circuit 158 shown in FIGS. 3 and 4. When so used, mode switches 182 are connected for serial operation, switch input line 72 is connected to switch input line 72A of high-joule switch 16A, load-line 76 is connected to ground, and trigger drive line 162 is connected to one-shot trigger 198. By using circuit 158 in serial triggering mode, the low-voltage triggering capability of one-shot trigger 198 may be used, and hence eliminate the delay inherent in optical triggering.

In operation, high-joule switch 16A is triggered by the method described in the discussion for the basic circuit. When high-voltage current appears on load-line 76A, the current activates one-shot delay 196, and one-shot delay 196 begins timing the desired pulse width. After one-shot delay 196 times out, it activates one-shot trigger 198 which, in turn, activates crowbar 200. The input current on switch input line 72A is thereupon substantially instantaneously shunted to ground, and the current flowing to high-joule switch 16A decreases to a value below its rated holding current. As a result, high-joule switch 16A turns off and produces the desired rectangular pulse.

CONCLUSION AND ALTERNATIVE EMBODIMENTS

Figure 6:
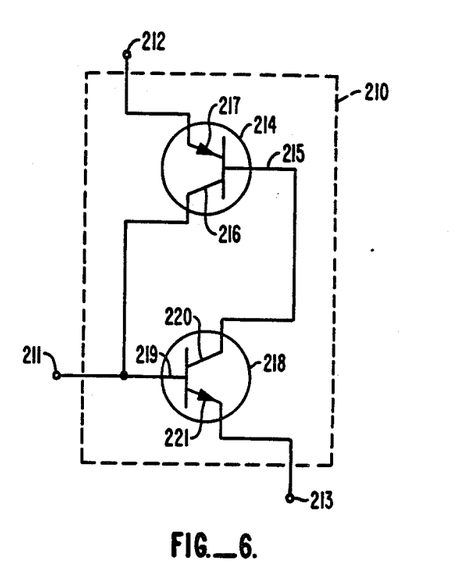
FIG. 6 is a schematic diagram of a two-transistor model of a semiconductor controlled rectifier.

While the above is a complete description of a preferred embodiment of the present invention, various modifications may be employed. For example, each SCR 80 may be replaced by an equivalent two-transistor SCR model 210 having a gate 211, an anode 212, and a cathode 213 as shown in FIG. 6. Gate 211, anode 212, and cathode 213 are equivalent to gate 84, cathode 88, and anode 92 of SCR 80 in FIG. 2.

As shown in FIG. 6, SCR model 210 comprises a PNP transistor 214 having a base 215, a collector 216, and an emitter 217, and an NPN transistor 218 having a base 219, a collector 220, and an emitter 221. The collector of NPN transistors 218 is connected to the base of PNP transistor 214, and the collector of PNP transistor 214 is connected to the base of NPN transistor 218. The base 219 and emitter 221 of NPN transistor 218, and the emitter 217 of PNP transistor 214 form the gate 211, cathode 213, and anode 212 of SCR model 210, respectively.

When an elctrical pulse is applied to the gate 211 of SCR model 211, transistor 218 turns on and forces collector 220 to a low potential. The low potential is coupled to base 215 and is sufficient to turn on transistor 214. The esulting current flowing from collector 216 is directed into base 219 of transistor 218 and sets up the conditions for sustained current flow. When the electrical pulse applied to gate 211 terminates, SCR model 210 remains in the conductive state provided that sufficient principal current is available to anode 212.

From the foregoing, it is apparent that the description should not be used to limit the scope of the invention which is properly described in the claims.

What is claimed is:

1. An apparatus for directing high voltage currents to a chemical solution comprising:
   means for storing an electrical charge;
   means for receiving the charge stored in the charge storing means;
   means for selecting an amount of charge stored in the charge storing means; and
   means for detecting the selected amount of charge stored in the charge storing means;
   means, responsive to the charge detecting means, for directing the charge stored in the charge storing means to the charge receiving means; and
   wherein the directing means includes a semiconductor controlled rectifier having an anode connected for receiving a current flowing from the charge storing means and a cathode connected for directing the charge stored in the charge storing means to the charge receiving means.

2. An apparatus for directing high voltage currents to a chemical solution comprising:
   means for storing an electrical charge;
   means for receiving the charge stored in the charge storing means;
   means for selecting an amount of charge stored in the charge storing means;
   means for detecting the selected amount of charge stored in the charge storing means;
   means, responsive to the charge detecting means, for directing the charge stored in the charge storing means to the charge receiving means; and
   wherein the directing means includes a plurality of transistors, the plurality of transistors having an input connected for receiving a current flowing from the charge storing means and an output connected for directing the charge stored in the charge storing means to the charge receiving means, the plurality of transistors being interconnected for forming a circuit capable of sustaining a current flow after an electrical pulse is applied thereto.

3. An apparatus for directing high voltage currents to a chemical solution comprising:
   means for storing an electrical charge;
   means for receiving the charge stored in the charge storing means;
   means for selecting an amount of charge stored in the charge storing means;
   means for detecting the selected amount of charge stored in the charge storing means;
   means, responsive to the charge detecting means, for directing the charge stored in the charge storing means to the charge receiving means; and wherein the directing means includes a PNP transistor and an NPN transistor, the collector of the PNP transistor being connected to the base of the NPN transistor, the collector of the NPN transistor being connected to the base of the PNP transistor, the emitter of the PNP transistor being connected for receiving a current flowing from the charge storing means, and the emitter of the NPN transistor being connected for directing the charge stored in the charge storing means to the charge receiving means.

4. An apparatus for directing high voltage currents to a chemical solution comprising:
  means for storing an electrical charge;
  means for receiving the charge stored in the charge storing means;
  means for selecting an amount of charge stored in the charge storing means;
  means for detecting the selected amount of charge stored in the charge storing means;
  means, responsive to the charge detecting means, for directing the charge stored in the charge storing means to the charge receiving means;
  wherein the charge storing means includes:
  means for storing an amount of charge above the selected amount; and
  means for discharging the charge storing means until the amount of charge stored in the charge storing means equals the selected amount whereby the detecting means detects the selected amount of charge stored in the charge storing means and the directing means directs the charge stored in the charge storing means to the charge receiving means in response thereto.

5. An apparatus for directing high voltage currents to a chemical solution comprising:
  a first semiconductor controlled rectifier having a gate, an anode for receiving a high-voltage current, and a cathode for emitting a high-voltage current;
  means, connected to the anode and to the cathode, for shunting the first semiconductor controlled rectifier, the shunting means including a metal oxide varistor connected in series with a capacitor; and
  means, connected to the gate, for triggering the first semiconductor controlled rectififer whereby a high voltage current flows from the anode to the cathode thereof.

6. The apparatus according to claim 5 wherein the triggering means includes means for storing an electrical charge for triggering the first semiconductor controlled rectifier, the amount of charge stored being proportional to the high voltage current received by the anode of the first semiconductor controlled rectifier.

7. The apparatus according to claim 5 further comprising:
  a second semiconductor controlled rectifier having a gate, an anode being coupled for receiving the high-voltage current emitted from the cathode of the first semiconductor controlled rectifier and a cathode for emitting a high-voltage current;
  means, connected to the anode and to the cathode of the second semiconductor controlled rectifier, for shunting the second semiconductor controlled rectifier, the shunting means including a metal oxide varistor connected in series with a capacitor; and
  means, connected to the gate of the second semiconductor controlled rectifier, for triggering the second semiconductor controlled rectifier whereby a high voltage current flows from the anode to the cathode thereof when a high-voltage current is emitted from the cathode of the first semiconductor controlled rectifier.

8. The apparatus according to claim 7 further comprising means, connected to the first and second semiconductor controlled rectifier triggering means, for substantially simultaneously triggering the first and second semiconductor controlled rectifiers.

9. The apparatus according to claim 7 further comprising means, connected to the first and second semiconductor controlled rectifier triggering means, for serially triggering the first and second semiconductor controlled rectifiers.

10. The apparatus according to claim 7 wherein the first semiconductor controlled rectifier triggering means includes a gate resistor connected to the gate of the first semiconductor controlled rectifier and a gate capacitor connected in series therewith, and wherein the second semiconductor controlled rectifier triggering means includes a gate resistor connected to the gate of the second semiconductor controlled rectifier and a gate capacitor connected in series therewith.

11. The apparatus according to claim 10 further comprising means, connected to the gate capacitors of the first and second semiconductor controlled rectifier triggering means, for providing a voltage pulse simultaneously thereto for substantially simultaneously triggering the first and second semiconductor controlled rectifiers, so that a high-voltage current flows from the anode of the first semiconductor controlled rectifier through the first and second semiconductor controlled rectifiers and is emitted by the cathode of the second semiconductor controlled rectifier.

12. The apparatus according to claim 10 wherein the first semiconductor controlled rectifier triggering means further comprises:
  a ground resistor connected in series with the gate capacitor and the gate resistor thereof, the ground potential being connected to a ground potential;
  means for storing a sufficient amount of electric charge in the gate capacitor to trigger the first semiconductor controlled rectifier when the gate capacitor is discharged; and
  means for discharging the gate capacitor when the cathode of the first semiconductor rectifier is connected to a substantially ground potential.

13. The apparatus according to claim 12 wherein the cathode of the second semiconductor controlled rectifier is connected to a substantially ground potential and further comprising means, connected to the capacitor of the second semiconductor controlled rectifier triggering means, for providing a voltage pulse thereto for triggering the second semiconductor controlled rectifier whereby the anode thereof assumes a substantially ground potential which is communicated to the cathode of the first semiconductor controlled rectifier, the first semiconductor controlled rectifier being triggered in response thereto.

14. An apparatus for directing a high voltage current to a chemical solution comprising:
  a first semiconductor controlled rectifier having a gate, an anode for receiving a high voltage current, and a cathode for emitting a high-voltage current;
  means, connected to the gate, for triggering the semiconductor controlled rectifier whereby a high voltage current flows from the anode to the cathode thereof;

a timer connected to the cathode;

means, connected to the timer for substantially instantaneously suppressing the high voltage current flowing through the anode of the first semiconductor controlled rectifier a predetermined interval of time after current begins to flow through the cathode so that the current flowing through the cathode of the first semiconductor controlled rectifier forms a generally rectangular pulse.

15. The apparatus according to claim 14 wherein the timer includes a one-shot delay.

16. A method for directing a high-voltage current to a chemical solution comprising the steps of:

connecting an electrical charge storing device for flowing current to the anode of a first semiconductor controlled rectifier;

connecting the cathode of the first semiconductor controlled rectifier for communicating a current to the chemical solution;

applying an electrical pulse to the gate of the first semiconductor controlled rectifier sufficient to render the first semiconductor controlled rectifier conductive;

directing the electrical charge flowing through the first semiconductor controlled rectifier to the chemical solution;

detecting a conductive state of the first semiconductor controlled rectifier to the chemical solution;

detecting a conductive state of the first semiconductor controlled rectifier;

measuring a predetermined time interval after detecting the conductive state of the first semiconductor controlled rectifier; and suppressing the current flowing through the first semiconductor controlled rectifier at the end of the predetermined time interval.

17. The method of claim 16 further comprising the step of limiting the potential at the cathode of the first semiconductor controlled rectifier.

18. The method of claim 16 further comprising:

connecting the anode of a second semiconductor controlled rectifier for receiving the current flowing through the cathode of the first semiconductor controlled rectifier;

connecting the cathode of the second semiconductor controlled rectifier for communicating a current to the chemical solution; and applying an electrical pulse to the gates of the first and second semiconductor controlled rectifiers sufficient to render the first and second semiconductor controlled rectifiers conductive; and directing the electrical charge flowing through the first and second semiconductor controlled rectifiers to the chemical solution.

19. The method of claim 18 wherein the step of applying the electrical pulse comprises the step of applying the electrical pulse substantially simultaneously to the gates of the first and second semiconductor controlled rectifiers.

20. The method of claim 18 further comprising the step of limiting the potential at the cathode of the second semiconductor controlled rectifier.

21. The method of claim 20 wherein the step of limiting the potential comprises the step of limiting the potential of the cathode of the second semiconductor controlled rectifier to a substantially ground potential.

22. The method of claim 21 wherein the pulse applying step comprises the steps of:

connecting the gate of the first semiconductor controlled rectifier to a capacitance capable of triggering the first semiconductor controlled rectifier when the capacitance is discharged; and discharging the capacitance.

23. The method of claim 21 further comprising the steps of:

communicating the potential at the anode of the second semiconductor controlled rectifier to the gate of the first semiconductor controlled rectifier;

applying an electrical pulse to the gate of the second semiconductor controlled rectifier sufficient to render the second semiconductor controlled rectifier conductive, whereby the substantially ground potential at the cathode thereof is communicated to the anode of the second semiconductor controlled rectifier and the gate of the first semiconductor rectifier, the substantially ground potential at the gate of the first semiconductor controlled rectifier discharging the capacitance to render the first semiconductor rectifier conductive.

24. A method for directing a high-voltage current to a chemical solution comprising the steps of:

interconnecting a plurality of transistors for forming a circuit capable of sustaining a current flowing from an input terminal thereof to an output terminal thereof after applying an electrical pulse thereto;

connecting the input terminal of the circuit to a charge storing device;

connecting the output terminal of the circuit for communicating a current flowing therefrom to the chemical solution;

applying an electrical pulse to the circuit to initiate a sustained current flow therethrough;

directing the current flowing from the output terminal of the circuit to the chemical solution;

detecting at the output terminal a conductive state of the plurality of transistors;

measuring a predetermined time interval after detecting the sustained conductive state of the plurality of transistors; and suppressing the current flowing through the input terminal at the end of the predetermined time interval.

25. The apparatus according to claim 15 wherein the suppressing means comprise a second semiconductor controlled rectifier having a gate, a cathode, and an anode connected to the cathode of the first semiconductor controlled rectifier; and means, connected to the one-shot delay and to the gate of the second semiconductor controlled rectifier, for triggering the second semiconductor controlled rectifier in response to signals received from the one-shot delay, so that current flows through the second semiconductor controlled rectifier and substantially and instantaneously suppresses the high voltage current flowing through the anode of the first semiconductor controlled rectifier below the rated holding current for the first semiconductor controlled rectifier.

26. An apparatus for directing high voltage currents to a chemical solution comprising:

means for storing an electrical charge;

means for receiving the charge stored in the charge storing means;

means for selecting an amount of charge stored in the charge storing means;

means for detecting the selected amount of charge stored in the charge storing means; and a first semiconductor controlled rectifier having an anode connected for receiving a current flowing from the charge storing means and a cathode connected for directing the charge stored in the charge storing means to the charge receiving means.

27. The apparatus according to claim 26 wherein the charge storing means includes means for storing an amount of charge above the selected amount, and further comprising:

means for discharging the charge storing means until the amount of charge stored in the charge storing means equals the selected amount whereby the detecting means detects the selected amount of charge stored in the charge storing means, and the first semiconductor controlled rectifier directs the charge stored in the charge storing means to the charge receiving means.

28. The apparatus according to claim 26 further comprising means for limiting the potential at the cathode of the first semiconductor controlled rectifier.

29. The apparatus according to claim 26 further comprising:

a second semiconductor controlled rectifier having an anode connected for receiving current flowing through a cathode of the first semiconductor controlled rectifier and having a cathode connected for communicating a current to the chemical solution; and means for applying an electrical pulse to the gates of the first and second semiconductor controlled rectifiers, the electrical pulse being sufficient to render the first and second semiconductor controlled rectifiers conductive so that current flows from the electrical charge storing device to the chemical solution.

30. The apparatus according to claim 29 wherein the electrical pulse applying means further comprises means for applying the electrical pulse substantially simultaneously to the gates of the first and second semiconductor controlled rectifier.

31. The apparatus according to claim 29 wherein the electrical pulse applying means further comprises means for serially applying the electrical pulse to the gates of the first and second semiconductor controlled rectifiers.

32. The apparatus according to claim 29 further comprising means, coupled to the cathode of the second semiconductor controlled rectifier, for limiting the potential at the cathode of the second semiconductor controlled rectifier.

33. The apparatus according to claim 32 wherein the limiting means limits the potential at the cathode of the second semiconductor controlled rectifier to a substantially ground potential.

34. The apparatus according to claim 33 wherein the electrical pulse applying means further comprises:

a capacitance connected to the gate of the first semiconductor controlled rectifier, the capacitance being capable of triggering the first semiconductor controlled rectifier when the capacitance is discharged; and means, coupled to the capacitance, for discharging the capacitance.

35. The apparatus according to claim 34 further comprising:

means for communicating the potential at the anode of the second semiconductor controlled rectifier to the gate of the second semiconductor controlled rectifier; and wherein the electrical pulse applying means applies an elctrical pulse to the gate of the second semiconductor controlled rectifier to render the second semiconductor controlled rectifier conductive, so that the substantially ground potential at the cathode of the second semiconductor controlled rectifier is communicated to the anode of the second semiconductor rectifier and to the gate of the first semiconductor controlled rectifier, the substantially ground potential at the gate of the first semiconductor controlled rectifier discharging the capacitance to render the first semiconductor controlled rectifier conductive.

* * * * *